United States Patent [19]

Miraki

[11] Patent Number: 5,324,269
[45] Date of Patent: Jun. 28, 1994

[54] FULLY EXCHANGEABLE DUAL LUMEN OVER-THE-WIRE DILATATION CATHETER WITH RIP SEAM

[75] Inventor: Manouchehr Miraki, Corona, Calif.

[73] Assignee: Baxter International Inc., Deerfield, Ill.

[21] Appl. No.: 893,588

[22] Filed: Jun. 2, 1992

Related U.S. Application Data

[63] Continuation of Ser. No. 762,827, Sep. 19, 1991, abandoned.

[51] Int. Cl.$^5$ ............................................. A61M 5/178
[52] U.S. Cl. ........................................ 604/160; 604/96
[58] Field of Search ................. 604/96, 160, 161, 102, 604/164

[56] References Cited

U.S. PATENT DOCUMENTS

| | | |
|---|---|---|
| 705,346 | 7/1902 | Hamilton . |
| 1,690,995 | 11/1928 | Pratt . |
| 3,633,586 | 1/1972 | Sheridan .............................. 604/96 |
| 3,853,130 | 12/1974 | Sheridan . |
| 4,175,564 | 11/1979 | Kwak . |
| 4,569,347 | 2/1986 | Frisbie . |
| 4,652,258 | 3/1987 | Drach . |
| 4,748,982 | 6/1988 | Horzewski et al. . |
| 4,762,129 | 8/1988 | Bonzel . |
| 4,776,846 | 10/1988 | Wells ................................... 604/161 |
| 4,881,547 | 11/1989 | Danforth . |
| 4,888,000 | 12/1989 | McQuilkin et al. .................. 604/160 |
| 4,943,278 | 7/1990 | Euteneuer et al. . |
| 4,944,745 | 7/1990 | Sogard et al. . |
| 4,976,690 | 12/1990 | Solar et al. . |
| 4,983,167 | 1/1991 | Sahota ................................... 604/96 |
| 4,988,356 | 1/1991 | Crittenden et al. .................. 604/96 |
| 5,029,591 | 7/1991 | Tevies ................................... 604/96 |
| 5,071,405 | 12/1991 | Piondak et al. ....................... 604/96 |
| 5,135,535 | 8/1992 | Kramer . |

FOREIGN PATENT DOCUMENTS

| | | |
|---|---|---|
| 93887 | 11/1983 | European Pat. Off. . |
| 121533 | 10/1984 | European Pat. Off. . |
| 0166212 | 1/1986 | European Pat. Off. . |
| 249456 | 12/1987 | European Pat. Off. . |
| 299158 | 1/1989 | European Pat. Off. . |
| 309754 | 4/1989 | European Pat. Off. . |
| 321648 | 6/1989 | European Pat. Off. . |
| 420486 | 9/1989 | European Pat. Off. . |
| 3080873 | 8/1990 | European Pat. Off. . |
| 386408 | 9/1990 | European Pat. Off. . |
| 0388112 | 9/1990 | European Pat. Off. . |
| 399712 | 11/1990 | European Pat. Off. . |
| 434324 | 6/1991 | European Pat. Off. . |
| 435157 | 7/1991 | European Pat. Off. . |
| 3320710 | 6/1983 | Fed. Rep. of Germany . |
| 3935579 | 8/1991 | Fed. Rep. of Germany . |
| 2597350 | 4/1987 | France . |
| 2033236 | 5/1980 | United Kingdom . |
| WO86/01414 | 3/1986 | World Int. Prop. O. . |
| WO86/07267 | 12/1986 | World Int. Prop. O. . |
| WO88/00071 | 1/1988 | World Int. Prop. O. . |

Primary Examiner—Paul J. Hirsch
Attorney, Agent, or Firm—Debra D. Condino; Raymond Sun

[57] ABSTRACT

A fully exchangeable over-the-wire dilatation catheter disclosed having an expandable balloon mounted on the distal end of a flexible, elongate tubular shaft provided with first and second through lumens. The first lumen traverses the longitudinal extent of the tubular shaft and is sealingly connected to the expandable balloon. The second lumen is adapted to slidingly receive a guidewire throughout the longitudinal extent of the tubular shaft and through the interior of the expandable balloon. The tubular shaft is also provided with a longitudinal rip seam extending into the second lumen from the proximal portion of the tubular shaft to a point adjacent the distal end of the tubular shaft. The rip seam may be provided with one or more side access ports into the second guidewire lumen and enables the catheter to be peeled from the guidewire during removal and exchange procedures without the need for docking a guidewire extension. The guidewire may be threaded through the side access ports in a variety of manners as desired. Associated procedures for utilizing the dilatation catheters are also disclosed.

19 Claims, 4 Drawing Sheets

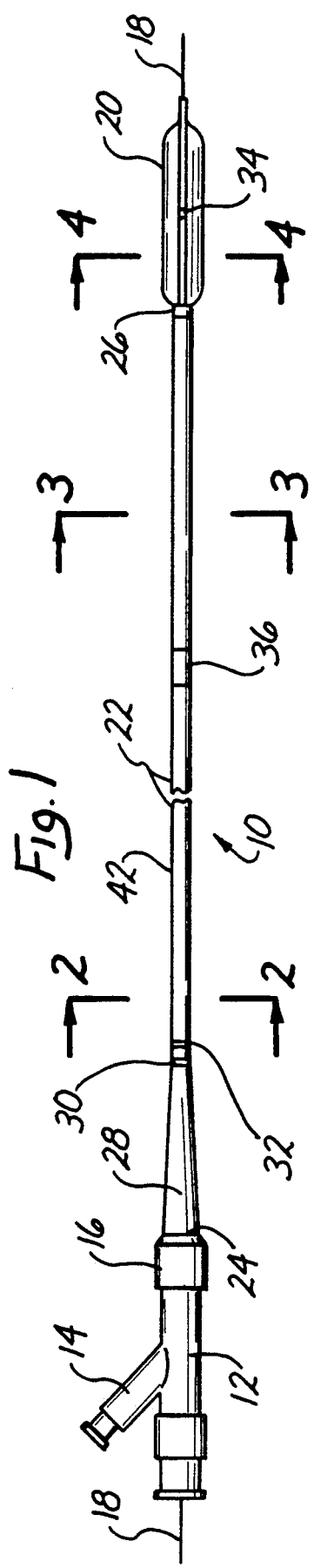
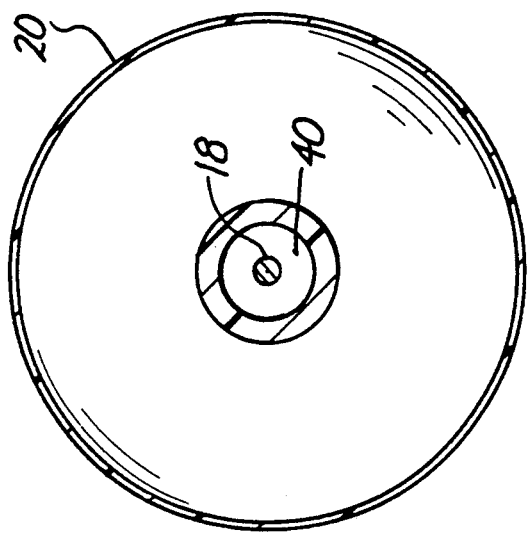
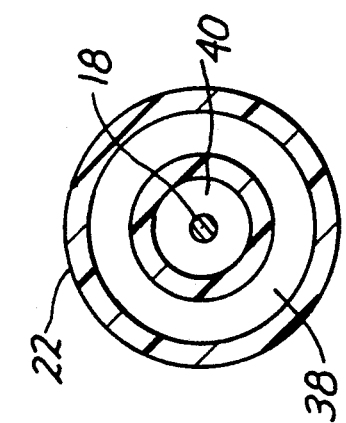
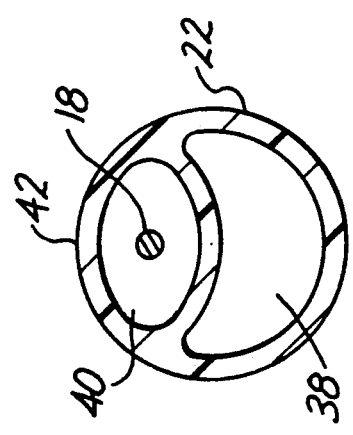
Fig. 1
Fig. 4
Fig. 3
Fig. 2

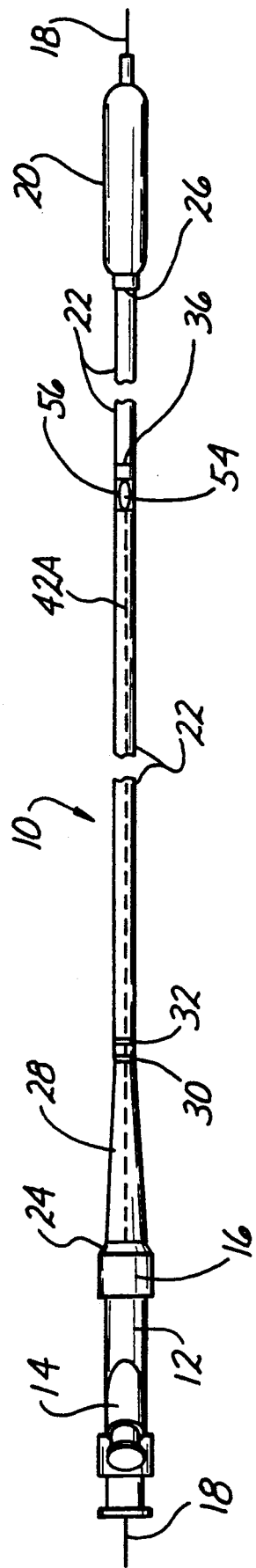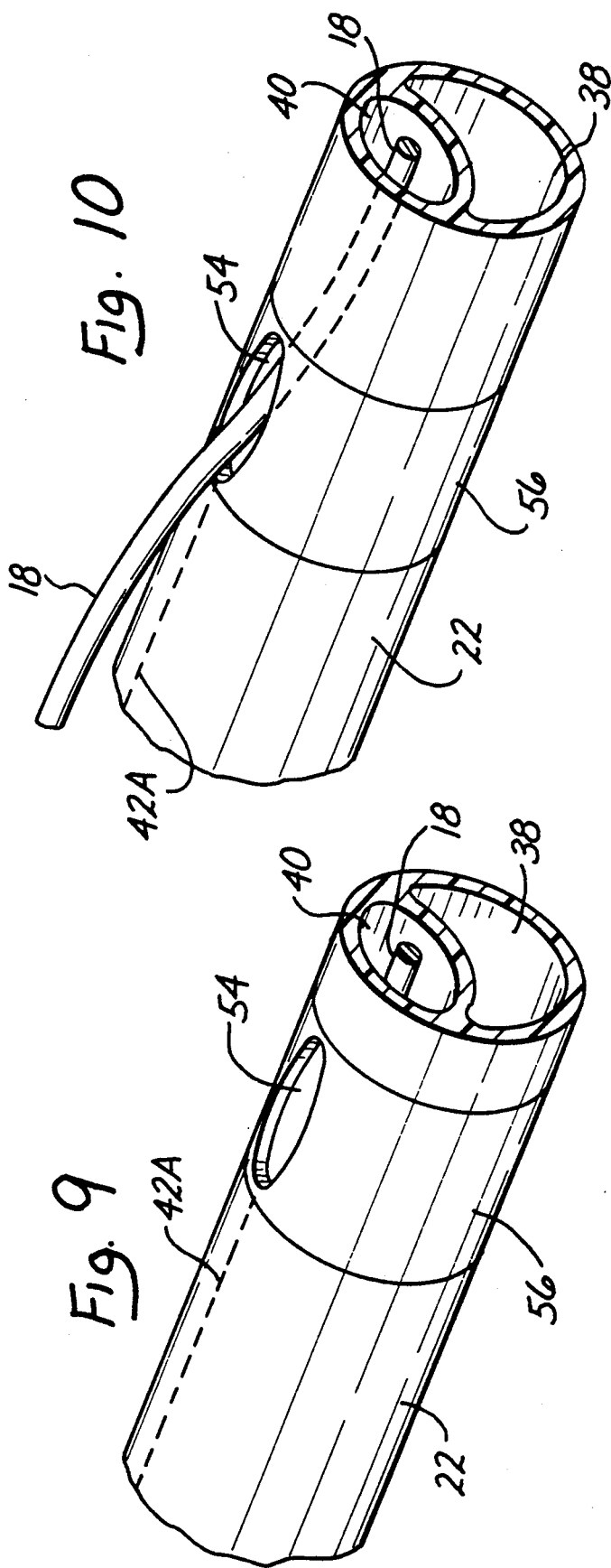

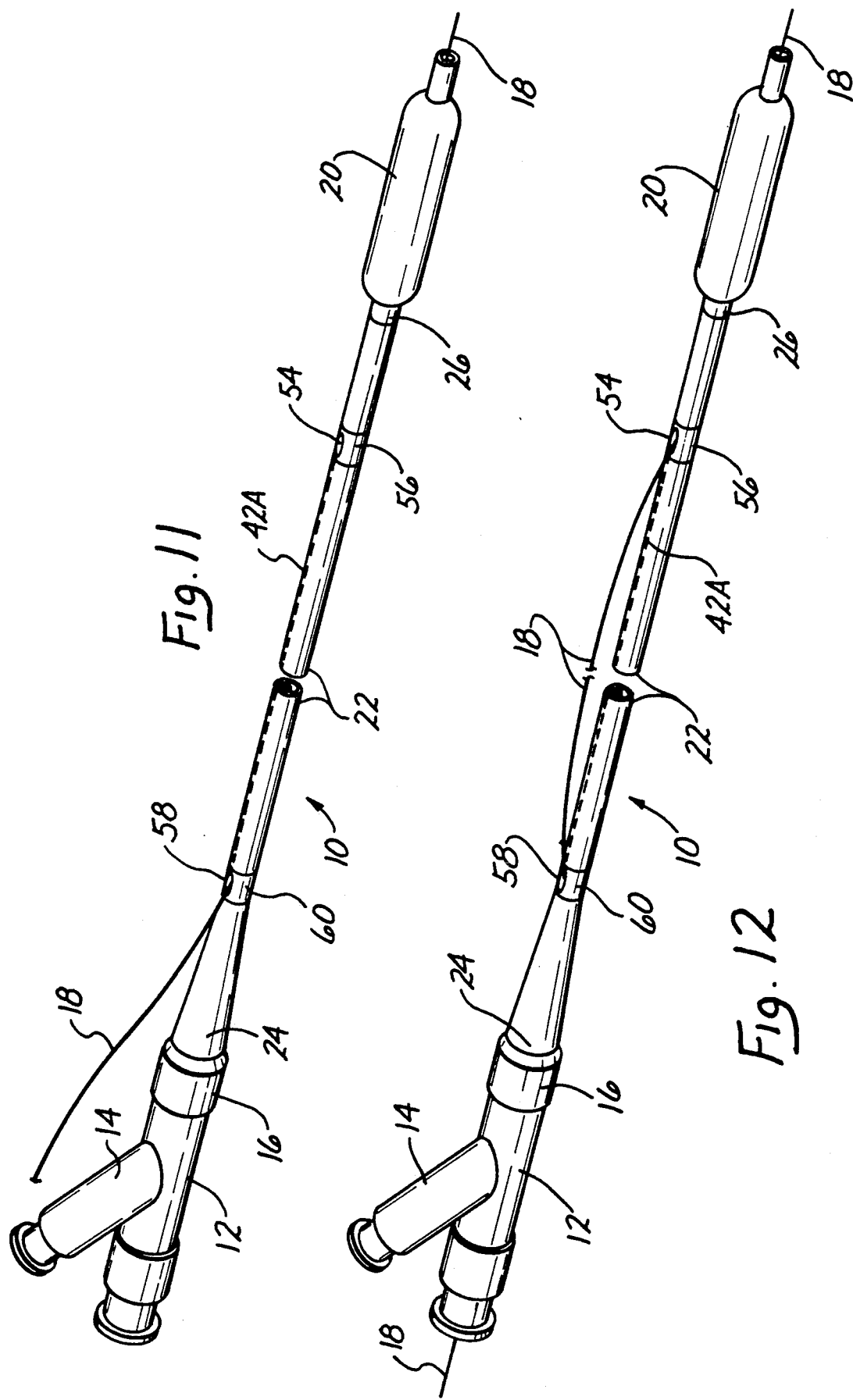

FULLY EXCHANGEABLE DUAL LUMEN OVER-THE-WIRE DILATATION CATHETER WITH RIP SEAM

This is a continuation, of application Ser. No. 07/762,827 filed on Sep. 19, 1991 now abandoned.

FIELD OF THE INVENTION

The present invention relates in general to the field of dilatation or balloon catheters employed in the treatment of vascular diseases. More particularly, the present invention relates to a dual lumen over-the-wire balloon catheter provided with a longitudinal rip seam extending along a majority of the length of its guidewire lumen from its proximal opening or adjacent thereto to a position adjacent its distal end or its dilatation balloon to facilitate the removal or exchange of the catheter assembly without docking a guidewire extension.

BACKGROUND OF THE INVENTION

A principle goal of modern medicine has been the reduction of trauma associated with various surgical procedures. When surgical invasiveness and trauma are reduced the associated surgical complications are correspondingly reduced. As a result, the less invasive the surgical procedure the greater the chances for a rapid, uncomplicated recovery. A recent successful development in the field of less invasive surgery is the medical procedure known as angioplasty. Angioplasty has become a widely accepted method for opening obstructions or stenoses throughout the vascular system, particularly in the coronary arteries.

The most common form of angioplasty practiced to date is known as percutaneous transluminal coronary angioplasty (PTCA). In virtually all forms of this procedure a dilatation catheter having an inflatable balloon at its distal end is guided through the patient's artery and the balloon is positioned across the stenosis. Once in place the balloon is inflated for a brief period of time in order to displace or deform the occluding lesion. After the stenosis has been opened and adequate blood flow has been reestablished the catheter is withdrawn. In this manner, it is possible to open blocked coronary arteries through a small vascular incision without the serious risks and complications previously associated with open heart surgery.

In most forms of angioplasty the dilatation catheter is guided into position through the patient's arteries utilizing a very small diameter flexible guidewire. Typically, guidewires are formed of surgical grade stainless steel having a diameter on the order of 0.010 to 0.015 inches and an overall length of approximately 175 cm. The distal end of the guidewire is extremely flexible and may be formed as a coil of very small diameter wire to enable the cardiac physician to direct the guidewire along the branched and convoluted arterial pathway as the guidewire is advanced to the target site. Once the guidewire is positioned across the lesion an appropriately sized dilatation catheter is advanced "over-the-wire". At this point in the procedure the dilatation balloon is in a deflated configuration having a minimal cross-sectional diameter which facilitates its positioning across the lesion prior to inflation. At various times throughout the procedure radiopaque dyes are injected into the artery to enable the cardiac physician to visualize the catheter and target vascular pathway on a fluoroscope.

An undesirable complication associated with the utilization of such "over-the-wire" dilatation catheters is the need to extend the guidewire outside of the patient's body a sufficient distance to enable the over-the-wire catheter to be threaded onto the guidewire without disturbing the positioning of the guidewire across the target lesion. Typically, a guidewire extension is "docked" or affixed to the proximal end of the guidewire in order to provide the additional length necessary to thread the guidewire into the catheter. As the typical dilatation catheter ranges in length from 120 cm to 160 cm the guidewire extension can be quite long and awkward to manipulate as it extends outside the patient's body. Alternatively, an exceptionally long guidewire on the order of 300 cm in length may be positioned initially and subsequently exchanged with a shorter, easier to handle guidewire after positioning of the catheter. In either case, an additional medical assistant may be necessary solely to monitor or manipulate the guidewire or its extension. Moreover, the junction between the docked guidewire end and the docked extension may interfere with the smooth advancement of the catheter along the guidewire decreasing the physician's control of the procedure.

A number of alternative dilatation catheter designs have been developed in an attempt to reduce or eliminate these problems. For example, "fixed-wire" dilatation catheters incorporating an internally fixed guidewire or stiffening element have been utilized with some degree of success. In addition to eliminating the need for guidewire extensions, these fixed-wire designs are smaller in diameter than their over-the-wire counterparts because the balloon inflation lumen is also utilized to contain the fixed guidewire. As a result, these designs are quite maneuverable and relatively easy to position. However, the most significant drawback associated with fixed-wire catheter designs is the inability to retain guidewire access to the target site while removing the catheter. Removal or replacement of a balloon catheter is not an uncommon occurrence during balloon angioplasty. Should it become necessary to perform such a removal or exchange procedure the fixed guidewire also must be removed simultaneously. This greatly complicates reaccessing the lesion with a subsequent device if desired.

Similarly, an additional drawback of fixed-wire catheter designs is the inability to exchange the guidewire. Though relatively rare, replacement of a guidewire is sometimes required when the original wire is broken or defective, or when the wire tip must be reshaped to perform the procedure. With these fixed wire unitary designs the entire assembly must be removed forcing the vascular physician to renegotiate the arterial pathway with a new catheter and guidewire combination.

An alternative catheter design is the "monorail" variant of the over-the-wire system such as that disclosed in U.S. Pat. No. 4,762,129 issued Aug. 9, 1988 to Bonzel. This catheter design utilizes a conventional inflation lumen plus a relatively short parallel guiding or through lumen located at its distal end and passing through the dilatation balloon. This design enables the short externally accessible monorail or guidewire lumen to be threaded over the proximal end of a pre-positioned guidewire without the need for docking a guidewire extension. Additionally, because the guidewire lumen is quite short the guidewire remains external to all portions of the catheter proximal to the distal portion of the catheter and frictional drag along the guidewire lumen reportedly is reduced. Thus, it is possible to recross an acutely closed lesion or to exchange balloon catheters without losing guidewire access or docking an extension wire.

However, in spite of this success a significant disadvantage associated with monorail dilatation catheters is the difficulty in steering the catheter along the guidewire through tortuous or convoluted vascular pathways. Because the guidewire is not supported within the catheter it is possible to wrap the distal end of the catheter around the guidewire as vascular curves and junctions are traversed. Additionally, though it is possible to remove the guidewire and leave the monorail catheter in position, it is virtually impossible to replace or exchange the guidewire if necessary as it is impossible to reengage the distal monorail guidewire lumen once it is positioned in the patient's body.

A more recent attempt at dealing with these problems is disclosed in U.S. Pat. No. 4,988,356 issued Jan. 29, 1991 to Crittenden et al. This catheter and guidewire exchange system utilizes a connector fitting mounted on the proximal end o the catheter and a longitudinal slit formed in the catheter shaft and extending from the proximal end proximate the connector forward towards the distal end. A guide member mounted on the fitting directs the guidewire through the slit and into the guidewire lumen in response to relative movement of the guidewire or catheter. This system reportedly avoids the need for a long exchange wire as well as the problems of a monorail design yet it presents several drawbacks of its own. First, the additional exchange fitting adds complexity to the design and function of the catheter. Further, the added drag induced by the fitting as it spreads the slit during catheter movement reduces the feel and control of the catheter as it is advanced along the guidewire. Moreover, because the slit terminates at a position distally to the proximal end of the catheter it is not possible to completely remove the catheter from the guidewire in a simple procedure. Reengagement of the catheter on the guidewire is even more complex.

Accordingly, it is an object of the present invention to provide a dilatation balloon catheter design that can be fully exchanged easily without sacrificing guidewire access to a target lesion. A concurrent object of the present invention is to provide such a dilatation catheter that can traverse branched arteries and vascular curves and bends with the ease of an over-the-wire design.

It is a further object of the present invention to provide a dilatation catheter that facilities the exchange or replacement of a guidewire if necessary.

It is yet an additional object of the present invention to provide a dilatation catheter with all of the advantages and features of an over-the-wire design that also provides the ability to be removed from a pre-positioned guidewire rapidly and simply without utilizing a guidewire extension or long exchange wire.

It is an additional object of the present invention to provide a fully exchangeable over-the-wire balloon catheter which will allow for catheter exchange without the need for docking a guidewire extension or utilizing a long exchange wire.

SUMMARY OF THE INVENTION

These and other objects are achieved by the full exchangeable, dual lumen over-the-wire balloon catheter of the present invention which, in accordance with broad structural aspects thereof, includes two longitudinally aligned open lumens extending throughout the length of the catheter body. The shorter first lumen terminates at the proximal end of the dilatation balloon while the second lumen traverses the interior of the balloon and terminates at or slightly beyond the distal end of the balloon. The catheter is formed with a longitudinal rip seam extending into the second lumen from the proximal end of the lumen along the majority of its length to a position proximal to the dilatation balloon.

This unique construction allows the longer lumen to function as an over-the-wire guidewire lumen that can be removed from the proximal end of the guidewire with a simple peeling action to eliminate the need for a guidewire extension. Further, in the preferred embodiment of the present invention the rip seam terminates in a distally located side access port. Accordingly, where desired, the cardiac physician may insert the externally accessible proximal end of the pre-positioned guidewire into the distal opening of the longer guidewire lumen through the dilatation balloon and back out through the side access port of the longitudinal rip seam to exchange the catheter without docking a guidewire extension or replacing the guidewire with a longer exchange wire. Thus, the dilatation catheter of the present invention provides all of the positioning and maneuverability advantages of a traditional over-the-wire catheter while it also provides for complete and uncomplicated catheter or guidewire exchangeability.

In an alternative embodiment of the present invention an additional side access port is provided at the proximal end of the rip seam, downstream of any Y-connector or fitting that may be mounted on the proximal end of the catheter. Thus, the rip seam will extend longitudinally along the catheter between the two side access holes. This alternative embodiment allows the vascular physician to utilize the catheter in several different manners.

For example, during initial placement of the device the guidewire can be threaded completely through the guidewire lumen from its distal opening to its proximal opening or, in the alternative, the proximal end of the guidewire may exit the proximal side access port. In either configuration the guidewire provides an added degree of pushability to the guidewire catheter combination during placement of the device. Should removal or exchange of the catheter be necessary this alternative construction utilizing the proximal side access port as an exit for the proximal end of the guidewire facilitates utilization of the rip seam and removal of the catheter by eliminating the need to remove any proximal fitting. Alternatively, where the guidewire transverses the entire length of the guidewire lumen any fitting or Y-connector must be detached prior to utilizing the rip seam.

As before, a replacement catheter may be threaded on to the externally accessible proximal end of the pre-positioned guidewire by threading the guidewire through the distal outlet of the second longer lumen and back out through the first or distal side access port. However, with this alternative embodiment the proximal end of the guidewire may be reinserted into the guidewire lumen through the second or proximal side access port and back out through the Y-connector or fitting in a "semi-over-the-wire configuration." In this configuration back bleeding is reduced during the procedure and wire movement is simplified.

The rip seam in all embodiments may be formed by longitudinally weakening the wall of the catheter integral with the second longer guidewire lumen through any known manner including reduced wall thickness, partial transverse cutting, perforation, slitting or the like. Preferably, the rip seam will terminate in a side access port located proximally to the dilatation balloon and the guidewire lumen will be coaxially disposed within the first inflation lumen from at least this point onward to the distal end of the device.

This preferred coaxial construction of at least the distal portion of the catheter improves the maneuverability and reduces the profile of the device. Additionally, the distal portion of the catheter can be formed from relatively flexible low density materials as opposed to the preferably stiffer construction of the proximal majority of the device. Visual marking indices may be added to facilitate the location of the side access port and radiopaque markers may be incorporated adjacent to the inflation balloon as known in the art. Various stiffening elements including wires or a proximal hypotube may be incorporated into the apparatus to improve its pushability. However, such stiffening elements should be removable or configured to not interfere with the function of the rip seam.

Other features and advantages of the present invention will become apparent from the following detailed description, taken in conjunction with the accompanying drawings which illustrate, by way of example, the principles of the present invention.

BRIEF DESCRIPTION OF THE DRAWINGS

FIG. 1 is a partial fragmentary view in elevation of a fully exchangeable dual lumen over-the-wire dilatation catheter with a rip seam illustrating the principles of the present invention.

FIG. 2 is a sectional view of the dilatation catheter as seen along line 2—2 of FIG. 1.

FIG. 3 is a sectional view of the dilatation catheter as seen along the line 3—3 of FIG. 1.

FIG. 4 is a sectional view of the dilatation catheter as seen along the line 4—4 of FIG. 1.

FIG. 8 is a partial fragmentary top elevational view of an alternative embodiment of the fully exchangeable dual lumen over-the-wire catheter of the present invention illustrating additional features thereof.

FIG. 9 is an enlarged partial fragmentary view of a portion of the dilatation catheter of FIG. 8 illustrating an exemplary side access port.

FIG. 10 is an enlarged partial fragmentary view of a portion of the dilatation catheter of FIG. 8 illustrating a side access port in conjunction with an alternative guidewire placement.

FIG. 11 is a partial fragmentary perspective view of an alternative embodiment of the fully exchangeable dual lumen over-the-wire dilatation catheter of the present invention in combination with a guidewire.

FIG. 12 is a partial fragmentary perspective view of the alternative embodiment of FIG. 11 illustrating an alternative guidewire placement.

DETAILED DESCRIPTION

Figure 5:
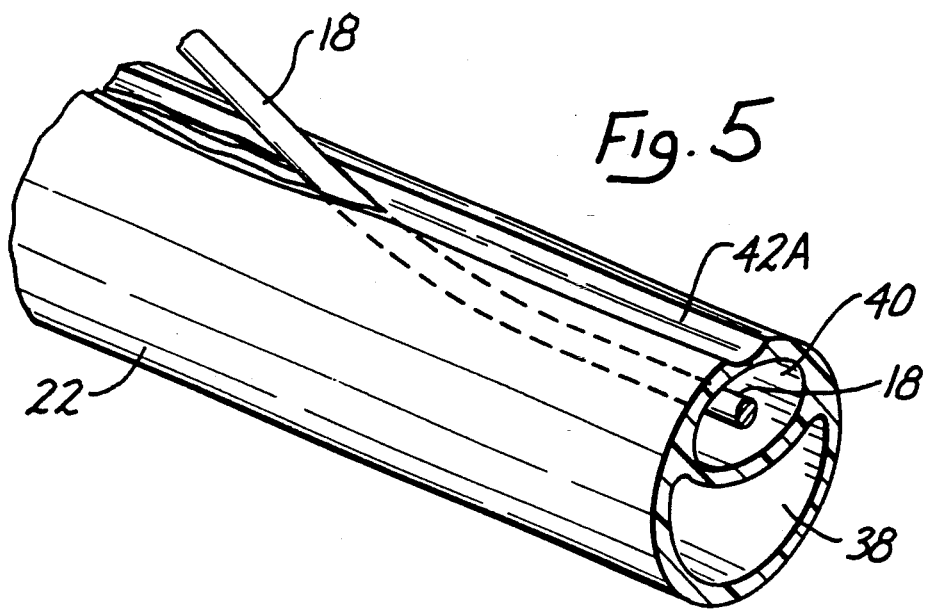
FIG. 5 is an enlarged partial fragmentary view of the fully exchangeable dual lumen over-the-wire dilatation catheter of the present invention in combination with a guidewire illustrating an embodiment of the rip seam.

Referring more particularly to the drawings in which similar elements are indicated by identical reference numerals. FIG. 1 illustrates an exemplary embodiment of the present invention including a catheter indicated generally by reference 10 mounted on a Y-connector 12 provided with an inflation port 14 and a compression hub 16 for sealing the catheter to Y-connector 12. A guidewire 18 extends proximally from Y-connector 12 and traverses the entire longitudinal extent of catheter 10. Catheter 10 includes an expandable or inflatable balloon 20 and a flexible, elongated tubular shaft 22 having a proximal end 24 adjacent compression hub 16 and a distal end 26 adjacent balloon 20. Though not essential to the practice of the present invention, catheter 10 also includes a tubular strain relief member 28 at its proximal end, depth markings 30 and 32 along the proximal portion of tubular shaft 22 and radiopaque marker 34 within balloon 20. Depth markings 30 and 32 enable the vascular physician to determine the relative positioning of catheter 10 within a patient while radiopaque marker 34 (formed of a precious metal such as gold or platinum) provides a clear visual image of the position of balloon 20 when viewed on a fluoroscope as known in the art.

Also, visible in FIG. 1 is fused joint 36 located along the distal portion of tubular shaft 22. As will be discussed in more detail below, though not essential to the practice of the present invention, it is preferred that the proximal majority of shaft 22 be formed of relatively high density material to enhance its stiffness and pushability. Similarly, it is preferred that the remaining distal portion of shaft 22 be formed of relatively low density material to increase its flexibility and maneuverability through tortuous vascular pathways such as the coronary arteries. Thus, fused joint 36 serves to bond these two materials together into a unitary construction. As those skilled in the art will appreciate, any form of medically acceptable secure joint is contemplated as being within the scope of the present invention while fusing the joint is preferred for manufacturing simplicity.

As shown in FIG. 2, catheter 10 is a dual lumen catheter provided with first and second lumens 38 and 40, respectively. Both lumens 38 and 40 extend throughout the longitudinal extent of tubular shaft 22 from proximal end 24 to distal end 26. Both lumens 38 and 40 are open at proximal end 24 and, in the exemplary embodiment of the present invention illustrated, first lumen 38 is connected in fluid conducting communication with inflation port 14 of Y-connector 12. At the distal end 26 of tubular shaft 22 first lumen 38 terminates in sealed fluid conducting communication with the interior of expandable balloon 20. Second lumen 40 is longer than first lumen 38 and is adapted to slidingly receive a guidewire 18 throughout its longitudinal extent from proximal end 24 and through the interior of expandable balloon 20. Thus, guidewire 18 is able to extend beyond both Y-connector 12 at the proximal end of catheter 10 and balloon 20 at the distal end of catheter 10.

As more clearly illustrated in FIG. 2, first and second lumens 38 and 40 may be disposed in a parallel or bi-lateral arrangement or, as shown in FIG. 3, a coaxial arrangement with second lumen 40 disposed within first lumen 38. It is preferred that at least the distal portion of second lumen 40 be coaxially disposed within the distal portion of first lumen 38. However, it is contemplated as being within the scope of the present invention to configure the dual lumen construction of tubular shaft 22 as a coaxial lumen throughout its longitudinal extent. Following the distal termination of first lumen 38, second lumen 40 continues to traverse the interior of balloon 20 as illustrated in the sectional view of FIG. 4. In this manner, first lumen 38 functions as an inflation lumen for inflating and deflating balloon 20 while second lumen 40 functions as an over-the-wire guidewire lumen.

However, unlike conventional over-the-wire guidewire catheters, the catheter of the invention is provided with a longitudinal rip seam 42 which extends into the second lumen 40 from the proximal end 24 of tubular shaft 22 to a position adjacent distal end 26. For example, in FIG. 1 rip seam 42 extends from proximal end 24 along shaft 22 (FIG. 2) to a position adjacent fused joint 36. Thus, as shown in FIGS. 2 and 3, rip seam 42 traverses the proximal majority of tubular shaft 22 yet is absent from the remaining distal portion thereof (FIG. 3). A wide variety of rip seam lengths and alternative embodiments of rip seam 42 are contemplated as being within the scope of the present invention.

Figure 6:
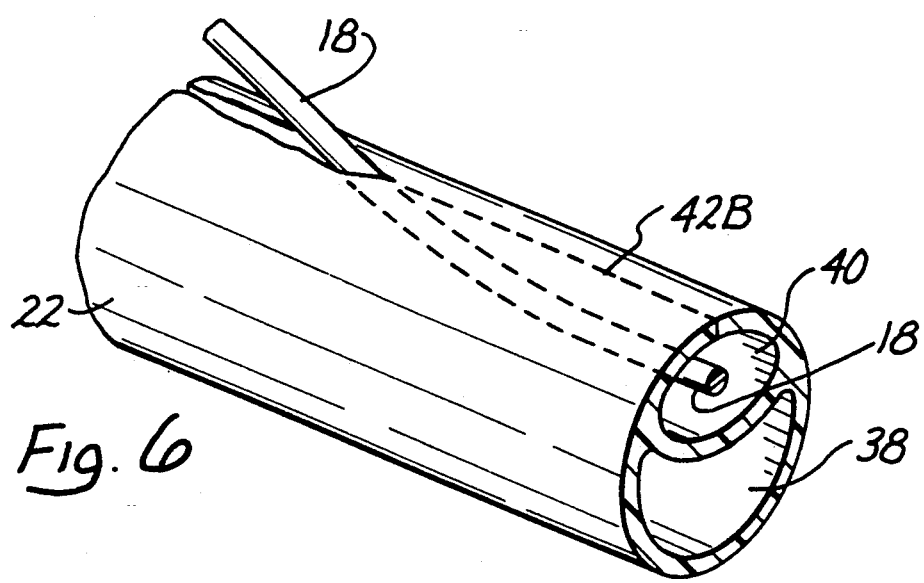
FIG. 6 is an enlarged partial fragmentary view of the fully exchangeable dual lumen dilatation catheter of the present invention in combination with a guidewire illustrating an alternative embodiment of the rip seam.
Figure 7:
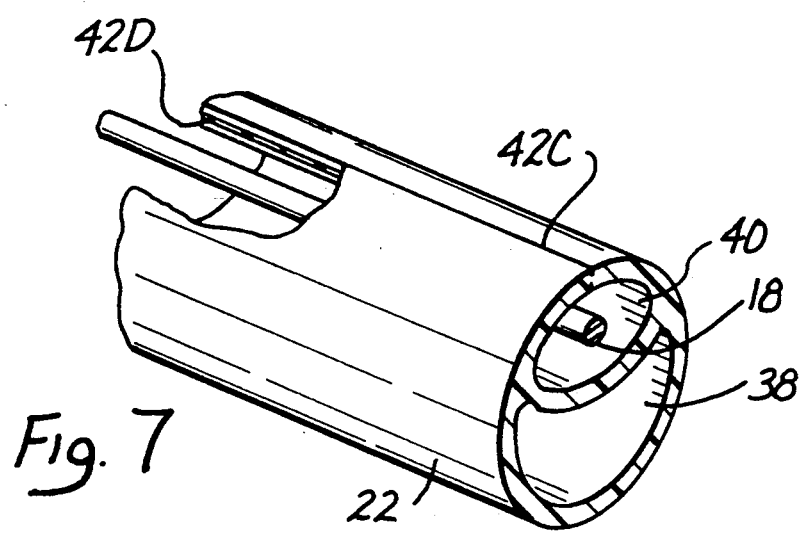
FIG. 7 is an enlarged partial fragmentary view of the fully exchangeable dual lumen dilatation catheter of the present invention in combination with a guidewire illustrating a still further alternative embodiment of the rip seam.

For example, the function of rip seam 42 is illustrated in the enlarged fragmentary view of FIG. 5. In FIG. 5 tubular shaft 22 of catheter 10 is shown being withdrawn along guidewire 18 by peeling the weakened wall material of reduced cross-sectional thickness wall material rip seam 42A from guidewire 18. Alternatively, in FIG. 6 rip seam 42B is formed from a longitudinally extending perforation through the wall material of second lumen 40. An additional alternative construction is illustrated in FIG. 7 where partial cuts 42C and 42D longitudinally extend along the wall of second lumen 40 in tubular shaft 22. Each partial cut 42C and 42D extends only part way through the wall thickness of second lumen 40. As those skilled in the art will appreciate, dual partial cuts are not essential to the practice of the present invention and a single partial cut will suffice to form rip seam 42. Each of the alternative forms of rip seam 42 functions in essentially the same manner allowing the vascular physician to withdraw catheter 10 along guidewire 18 by peeling guidewire 18 through rip seam 42.

In this manner, the over-the-wire dilatation catheter of the present invention provides the vascular physician with the ability to fully exchange the dilatation catheter without compromising guidewire access to a target lesion. For example, the fully exchangeable dilatation catheter 10 of the present invention may be inserted like a conventional over-the-wire catheter by threading the catheter guidewire lumen 40 along the guidewire 18 and advancing the catheter along a target vascular pathway to position the balloon 20 across a target lesion or stenosis. After the vascular physician has performed an angioplasty procedure by expanding and contracting the balloon across the stenosis the catheter may be withdrawn and removed from the patient by peeling the rip seam 42 from the proximal end of the guidewire positioned outside of the patient. By continuing to withdraw and peel the dilatation catheter along the guidewire the coaxial distal portion of the catheter may be removed from the patient and subsequently removed from the proximal portion of the guidewire without utilizing a docking extension or losing the positioning of the guidewire.

An additional feature of the present invention is illustrated in FIG. 8 where rip seam 42 is shown terminating in a contiguous side access port 54 in second lumen 40. Preferably, side access port 54 is located in a distal position along tubular shaft 22 remote from expandable balloon 20 at a point where second lumen 40 is directly adjacent to the wall of tubular shaft 22. For example, in FIG. 8 side access port 54 is positioned at fused joint 36. To assist the vascular physician in locating side access port 54, a distinctive visual marking 56 is provided to clearly indicate the position of side access port 54. It should be appreciated, that visual marking 56 is not essential to the practice to the present invention.

As illustrated in FIGS. 9 and 10, side access port 54 provides several additional advantages to the present invention. By clearly defining the distal termination of rip seam 42 side access port 54 provides the vascular physician with an additional degree of visual and tactile information regarding the progress of peeling guidewire 18 from second lumen 40 when withdrawing catheter 10 from a patient. Alternatively, should a vascular physician wish to exchange the dilatation catheter of the present invention with a second version having a different sized balloon 20 or to correct a nonfunctioning device, the physician may utilize side access port 54 as an exit from second lumen 40 to assist in threading catheter 10 onto the externally accessible end of guidewire 18 without the need for docking a guidewire extension. Thus, it is possible to remove and exchange the dilatation catheter of the present invention from a target vascular pathway by positioning and removing the catheter as previously discussed, then providing a second fully exchangeable dilatation catheter and threading the externally accessible proximal portion of the prepositioned guidewire through the distal portion of second lumen 40 and back outside access port 54, and then advancing this second catheter along the guidewire into position across the target stenosis.

An additional embodiment of the fully exchangeable over-the-wire dilatation catheter of the present invention is illustrated in FIGS. 11 and 12. In this embodiment a second or proximal side access port 58 is provided adjacent proximal end 24 of tubular shaft 22 and defines the proximal termination of rip seam 42. As with side access port 54, proximal side access port 58 is provided with its own visual marking 60 to aid in its location during utilization of catheter 10. As those skilled in the art will appreciate, angioplasty procedures are most often performed in darkened environments to enhance fluoroscopic visualization. Accordingly, visual markings 56 and 60, which may be formed in any manner known in the art including painting, etching, or embossing, may greatly assist the vascular physician in utilization of the apparatus.

In the alternative embodiment of the present invention illustrated in FIGS. 11 and 12 rip seam 42 longitudinally extends between side access ports 54 and 58 With a proximal termination distally of compression hub 16 on Y-connector 12. Accordingly, if desired, guidewire 18 may be threaded through second lumen 40 as previously described with the added ability to exit through second side access port 58 adjacent Y-connector 12. This configuration, as illustrated in FIG. 11, enables the vascular physician to remove catheter 10 from a patient by peeling rip seam 42 from guidewire 18 without removing Y-connector 12. Moreover, after exchanging or replacing the dilatation catheter with a second such device, the proximal portion of guidewire 18 may be reinserted into second lumen 40 through second side access port 58 and out through Y-connector 12. In this manner, a replacement dilatation catheter may be utilized in a semi-over-the-wire configuration with all of the advantages of an over-the-wire versus a monorail catheter design.

As previously noted, each of the embodiments of the present invention discussed herein may be formed from a variety of surgically acceptable flexible materials as known in the art. However, it is preferred that the proximal portion of tubular shaft 22 be formed of a relatively high density material such as polyethylene or polypropylene to provide added pushability and control in placing the catheter within a vascular pathway. For enhanced flexibility and maneuverability at the distal end of the catheter it is preferred that the remaining distal portion of the tubular shaft be formed of relatively low density material such as polyethylene or polypropylene. These two materials may be fused by thermal bonding to form the previously discussed fused joint 36. Preferably, fused joint 36 will be located approximately 30 cm from balloon 20 on an exemplary catheter having an overall length ranging from approximately 100 cm to 160 cm.

Additionally, it should be appreciated that various stiffening elements may be utilized in conjunction with the dilatation catheter of the present invention. For example, the proximal portion of tubular shaft 22 may be stiffened utilizing wires (not shown) or flexible metal tubes known as "hypotubes" (not shown) which are disposed along its longitudinal extent. However, such stiffening elements should be removable to avoid interference with the operation of rip seam 42. It should be appreciated that these exemplary materials, dimensions and construction techniques are illustrative of the principles of the present invention and that other alternative materials, dimensions and construction techniques may be utilized within the scope of the present invention.

In closing it is to be understood that the embodiments of the invention disclosed herein are illustrative of the principles of the invention and that other modifications may be employed which are within the scope thereof. Thus, by way of example, but not of limitation, the rip seam may be opened with a cutting instrument located on the Y-connector or an external fitting in a manner that will open the second guidewire lumen as the catheter is removed along the guidewire. Accordingly, the present invention is not limited to that precisely as shown and described in the specification.

What is claimed:

1. A fully exchangeable over-the-wire dilatation catheter comprising:
    an expandable balloon; and
    a flexible, elongate tubular shaft having a proximal end, a distal end, and first and second through lumens, each of said lumens in open extension from said proximal end to said distal end, said first lumen terminating in sealed fluid conducting communication with the interior of said expandable balloon at said distal end of said tubular shaft, said second lumen provided with a distal side access port disposed near said distal end proximal to said balloon, a proximal side access port disposed near said proximal end of said tubular shaft, with said tubular shaft having a longitudinal rip seam extending into said second lumen from said proximal end to a position near said distal end proximal to said balloon, said second lumen adapted to slidingly receive a guidewire throughout its longitudinal extent from said proximal end to said distal end and through said interior of said expandable balloon.

2. The fully exchangeable over-the-wire dilatation catheter of claim 1 wherein the proximal portion of said flexible, elongate tubular shaft is formed of relatively high density material to provide added stiffness and pushability.

3. The fully exchangeable over-the-wire dilatation catheter of claim 1 wherein the distal portion of said flexible, elongate tubular shaft is formed of relatively low density material to provide added flexibility and maneuverability.

4. The fully exchangeable over-the-wire dilatation catheter of claim 1 wherein the proximal majority of aid flexible, elongate tubular shaft is formed of relatively high density material, the remaining distal portion of said flexible, elongate tubular shaft is formed of relatively low density material, and said rip seam distally terminates at a position adjacent the distal portion of said relatively high density material.

5. The fully exchangeable over-the-wire dilatation catheter of claim 1 wherein said rip seam is formed from a longitudinally extending weakened wall in said tubular shaft.

6. The fully exchangeable over-the-wire dilatation catheter of claim 1 wherein said rip seam is formed from a longitudinally extending perforation in the wall of said tubular shaft.

7. The fully exchangeable over-the-wire dilatation catheter of claim 1 wherein said rip seam is formed from a longitudinally extending partially transverse slit in the wall of said tubular shaft.

8. The fully exchangeable over-the-wire dilatation catheter of claim 1 further comprising visual marking means disposed adjacent to each of said side access pots.

9. The fully exchangeable over-the-wire dilatation catheter of claim 1 wherein said second lumen is coaxially disposed within said first lumen at all points distal to said distal side access port.

10. The fully exchangeable over-the-wire dilatation catheter of claim 1 further comprising at least one radiopaque marker disposed adjacent to said expandable balloon.

11. The fully exchangeable over-the-wire dilatation catheter of claim 1 wherein the rip seam extends from the proximal end to the distal side access port.

12. The fully exchangeable over-the-wire dilatation catheter of claim 1 wherein the rip seam extends from the proximal side access port to the distal side access port.

13. A method for removing a fully exchangeable over-the-wire dilatation catheter from a guidewire positioned within a target vascular pathway of a patient, said method comprising the steps of:
    providing the fully exchangeable over-the-wire dilatation catheter of claim 1;
    threading a guidewire along the longitudinal extent of the second lumen of said dilatation catheter;
    advancing the dilatation catheter and guidewire combination along said vascular pathway to a position across a stenosis in said target vascular pathway;
    performing an angioplasty procedure by expanding and contracting said balloon positioned across said stenosis;

withdrawing said dilatation catheter along said guidewire by peeling the rip seam of said tubular shaft form the externally accessible proximal end of said guidewire and continuing to withdraw said dilatation catheter while peeling said guidewire from said rip seam until the distal portion of said catheter is outside said patient; and removing the remaining portion of said catheter from said guidewire.

14. A method for removing and exchanging a fully exchangeable over-the-wire dilatation catheter from a guidewire positioned within a target vascular pathway of a patient and having a proximal guidewire portion located outside of said patient, said method comprising the steps of:

providing the fully exchangeable over-the-wire dilatation catheter of claim 1;

threading a guidewire along the longitudinal extent of the second lumen of said catheter;

advancing the dilatation catheter and guidewire combination along the vascular pathway of said patient to a position across a target stenosis;

performing an angioplasty procedure by expanding and contracting said balloon of said catheter;

withdrawing said catheter along said guidewire by peeling said rip seam from said proximal portion of said guidewire and continuing to withdraw said catheter while peeling said guidewire from said rip seam until the distal portion of said catheter is outside said patient;

removing the remaining distal portion of said catheter from said guide wire;

providing a second fully exchangeable over-the-wire dilatation catheter of claim 1;

threading the proximal portion of said guidewire through the distal end of the second lumen of said second catheter and out said distal side access port; and advancing said second catheter along said guidewire.

15. A method for removing and exchanging a fully exchangeable over-the-wire dilatation catheter from a guidewire positioned within a target vascular pathway of a patient and having a proximal guidewire portion located outside of said patient, said method comprising the steps of:

providing the fully exchangeable over-the-wire dilatation catheter of claim 1;

threading a guidewire along the longitudinal extent of the second lumen of said catheter;

advancing the dilatation catheter and guidewire combination along the vascular pathway of said pathway to a position across a target stenosis;

performing an angioplasty procedure by expanding and contracting said balloon of said catheter;

withdrawing said catheter along said guidewire by peeling said rip seam from said proximal portion of said guidewire and continuing to withdraw said catheter while peeling said guidewire from said rip seam until the distal portion of said catheter is outside said patient;

removing the remaining distal portion of said catheter form said guide wire;

providing a second fully exchangeable over-the-wire dilatation catheter of claim 1;

threading the proximal portion of said guidewire; and inserting said proximal portion of said guidewire into said proximal side access port and through the proximal end of said second lumen.

16. A method for removing and exchanging a fully exchangeable over-the-wire dilatation catheter from a guidewire positioned within a target vascular pathway of a patient and having a proximal guidewire portion located outside of said patient, said method comprising the steps of:

providing the fully exchangeable over-the-wire dilatation catheter of claim 1;

threading a guidewire along the longitudinal extent of the second lumen of said catheter;

advancing the dilatation catheter and guidewire combination along the vascular pathway of said patient to a position across a target stenosis;

performing an angioplasty procedure by expanding and contracting said balloon of said catheter;

withdrawing said catheter along said guidewire by peeling said rip seam from said proximal portion of said guidewire and continuing to withdraw said catheter while peeling said guidewire from said rip seam until the distal portion of said catheter is outside said patient;

removing the remaining distal portion of said catheter from said guide wire;

providing a second fully exchangeable over-the-wire dilatation catheter of claim 1;

threading the proximal portion of said guidewire through the distal end of the second lumen of said second catheter and out said proximal side access port; and advancing said second catheter along said guidewire.

17. A method for positioning a semi-over-the-wire dilatation catheter on a guidewire positioned within a target vascular pathway of a patient and having a proximal guidewire portion located outside of said patient, said method comprising the steps of:

threading said proximal guidewire portion into the distal end of the second lumen of the catheter of claim 12 and out through the distal side access port of said catheter;

advancing said catheter along said guidewire and into said patient; and threading said proximal portion of said guidewire into the proximal side access port of said catheter and out through the proximal end of said second lumen.

18. A method of exchanging a guidewire in a catheter positioned within a target vascular pathway of a patient, said method comprising the steps of:

threading a first guidewire through the second lumen of the dilatation catheter of claim 1;

positioning said first guidewire and dilatation catheter combination within the target vascular pathway of a patient so that the proximal side access port of said catheter remains outside said patient;

removing said first guidewire from said catheter; and threading a second guidewire into said proximal side access port and through said second lumen.

19. A method of exchanging a guidewire in a catheter positioned within a target vascular pathway of a patient, said method comprising the steps of:

threading a first guidewire through the second lumen of the dilatation catheter of claim 1;

removing said first guidewire from said catheter; and threading a second guidewire into said proximal end of said second lumen and through said second lumen.

* * * * *